United States Patent [19]

Deckner

[11] Patent Number: 4,690,815

[45] Date of Patent: Sep. 1, 1987

[54] METHOD FOR TESTING SKIN FOR PRESENCE OF MOISTURIZER

[75] Inventor: George E. Deckner, Westfield, N.J.

[73] Assignee: Charles of the Ritz Group Ltd., New York, N.Y.

[21] Appl. No.: 765,632

[22] Filed: Aug. 15, 1985

[51] Int. Cl.[4] .................... C12Q 1/58; G01N 33/62; G01N 33/68; G01N 33/48

[52] U.S. Cl. .......................... 424/9; 435/12; 435/14; 435/805; 436/86; 436/88; 436/95

[58] Field of Search ............ 435/10, 12, 14, 179, 435/805, 810; 436/86, 88, 95, 99; 422/56, 57; 424/7.1, 9

[56] References Cited

U.S. PATENT DOCUMENTS

| | | | |
|---|---|---|---|
| 3,145,086 | 8/1964 | Free et al. | 435/12 |
| 3,395,082 | 7/1968 | Mast | 435/12 |
| 3,427,225 | 2/1969 | Harvill et al. | 435/12 |
| 3,438,737 | 4/1969 | Atkinson et al. | 436/86 |
| 3,449,080 | 6/1969 | Edwards | 424/9 |
| 3,461,036 | 8/1969 | Harvill et al. | 435/12 |
| 3,814,668 | 6/1974 | Blake et al. | 435/14 |

*Primary Examiner*—Esther M. Kepplinger
*Attorney, Agent, or Firm*—Lerner, David, Littenberg, Krumholz & Mentlik

[57] ABSTRACT

A method for testing skin for presence of moisturizing substances is provided which method includes the steps of applying to the skin a moisturizer formulation which includes protein, urea and/or glucose and/or other reducing sugar such as fructose all of which bind with water and form a film or coating on the skin which inhibits moisture loss from the skin, and subsequently testing the skin for the presence of protein, urea and/or glucose and/or other reducing sugar remaining on the skin which is directly correlated to the amount of moisturizer formulation remaining on the skin. When it is determined through the testing that there has been at least a predetermined loss of protein, urea and/or glucose or other reducing sugar, additional moisturizer is then applied to the skin.

11 Claims, No Drawings

METHOD FOR TESTING SKIN FOR PRESENCE OF MOISTURIZER

FIELD OF THE INVENTION

The present invention relates to a method for testing skin for the presence of certain moisturizing substances such as protein, urea and/or glucose or other reducing sugar by the use of test strips sensitive to these materials.

BACKGROUND OF THE INVENTION

The presence of water in the outer dead layers of the epidermis is essential to prevent what is generally referred to as "dry skin". If water is depleted from the stratum corneum more rapidly than it is received from the lower layers of the epidermis, the skin becomes dehydrated and loses its flexibility. Moisturizing compositions are essential and quite effective in restoring water lost from the stratum corneum and thereby prevent the above conditions.

One of the more important properties of a moisturizer composition is its substantivity or staying power, that is, the ability to form a film or coating which will remain on the skin even after washing. The actives which may be present, such as protein, urea and/or glucose and/or other reducing sugars, bind with water and aid in forming the film or coating. However, many moisturizer compositions available today are non-greasy compositions which are difficult to detect once applied to the skin. Thus, the user of such compositions may not be aware that the moisturizing film or coating has been washed off or otherwise removed and as a result may develop dry skin. To avoid this problem many users of such moisturizer composition may randomly apply same to the skin several times throughout the day regardless of the substantivity of the moisturizing composition.

Until now, there was no known accurate, simple, quick technique available for determining the presence of moisturizer on the skin and when additional moisturizer is necessary to avoid dry skin and therefore should be applied.

DESCRIPTION OF THE INVENTION

In accordance with the present invention, a method is provided for determining the presence of moisturizing substances on skin, which method includes the steps of forming a moisturizer composition which includes one or more actives such as protein, urea and/or glucose and/or other reducing sugar or carbohydrate which binds with water, applying the moisturizer composition to desired areas of the skin to form a film or coating on the skin which inhibits moisture loss from the skin, and subsequently testing skin previously treated with such moisturizer composition for the presence of protein, urea and/or glucose and/or other reducing sugar or carbohydrate remaining on the previously treated skin the presence of which is directly correlated to the amount of moisturizer remaining on the skin.

The testing step for detecting the presence of actives such as protein, urea and/or glucose and/or other reducing sugar or carbohydrate is accomplished through the use of known test indicators for these materials. For example, the presence of protein on the skin as a result of the previous application of moisturizer composition may be detected through the use of the protein test device disclosed in the working Examples of U.S. Pat. No. 3,438,737 to Atkinson et al; the presence of urea on the skin as a result of the previous application of moisturizer composition may be detected through the use of the urea test device disclosed in the working Examples of U.S. Pat. Nos. 3,461,036 to Harvill et al, 3,427,225 to Harvill et al, 3,395,082 to Mast, and 3,145,086; and the presence of glucose and/or other reducing sugar on the skin as a result of the previous application of moisturizer may be detected through the use of the glucose test device disclosed in the working Example of U.S. Pat. No. 3,814,668 to Blake et al.

The moisturizer compositions may contain one or more actives such as the protein, urea and/or glucose and/or other reducing sugars or carbohydrates. Thus, the actual testing step carried out will vary depending upon which one or more of these indicators were present in the moisturizer composition as previously applied. For example, where only one of the above materials is present in the moisturizing composition, a single test strip device as disclosed in the appropriate patent for testing of the material, may be employed. Where two or more of protein, urea and/or glucose and/or other reducing sugar are present, then one or more appropriate test strips each separately or combined into a single test strip or device may be employed.

The moisturizer composition will contain at least one of the protein, such as albumin, urea and/or glucose and/or other reducing sugar such as fructose, lactose or maltose and may be of conventional composition. Thus, the moisturizer composition will contain from about 0.1 to about 10% and preferably from about 0.1 to about 2% by weight of a protein such as albumin, from about 0.1 to about 10% and preferably from about 0.1 to about 5% by weight urea, and from about 0.1 to about 10% and preferably from about 0.1 to about 5% by weight glucose or other reducing sugar. The protein, urea, glucose and/or other reducing sugar will serve to bind water and form a film or coating which may be occlusive and prevent loss of moisture from the skin. Each test strip or section of combined test strip will be specific to one of the above materials and will vary in color depending upon the concentration of these materials remaining on the skin. The actual color change or lack of color change obtained will determine whether additional moisturizer composition should be applied.

The moisturizer composition for use in the method of the invention may take the form of a cream or lotion and will include actives or highly effective moisture regulators based on naturally occurring carbohydrates, such as glucose and/or other reducing sugars, as well as proteins, such as serum albumin or egg albumin and/or urea which are similar to those found in the outer layers of skin. The actives combine with water to form an active complex in the form of a film or coating which effectively adheres to skin to assure sustained moisturizer activity. Such complex is even effective at low humidities when skin is most likely to suffer from dryness.

Employing the method of the invention, using the test strips described in the aforementioned patents, a person will be able to confirm the effectiveness of the moisturizer. The test strips react with the active complex contained in the cream or lotion to change color. To test, the subject merely wets the test strip and places it on his skin for 30 seconds or more. No color change in the test strip indicates reapplication of moisturizer is necessary. Where there is a color change in the test strip, such color change will be approximately proportioned to the amount of active complex remaining on the skin from previous applications of moisturizer compositions.

The moisturizer formulations employed in the method of the invention will also contain conventional moisturizer ingredients necessary in formulating a desirable product, such as, one or more diluents, thickeners, stabilizers, coloring agents, humectants, preservatives, emollients, bodying agents, sunscreen agents and the like. The moisturizer formulations of the invention may contain one or more diluents such as deionized water in an amount within the range of from about 40 to about 90% and preferably from about 50 to about 80% by weight, optionally one or more thickeners, such as magnesium aluminum silicate, Carbomer 934 and xanthan gum in an amount within the range of from about 0.1 to about 2% and preferably from about 0.1 to about 0.5% by weight, optionally one or more skin protecting agents, such as panthenol, which serves as a skin moisturizer and humectant, in an amount within the range of from about 0.1 to about 5% and preferably from about 0.1 to about 1% by weight, one or more other humectants such as polyethylene glycols (for example, Carbowax 400), sodium 2-pyrrolidone carboxylic acid, sorbitol, propylene glycol or glycerine in an amount within the range of from about 1 to about 20% and preferably from about 1 to about 5% by weight, one or more preservatives such as parabens including methyl paraben, propyl paraben, butyl paraben, Glydant (dimethyldimethoyl hydantoin), benzyl alcohol, imidazolidinyl urea and the like usually employed in amounts within the range of from about 0.1 to about 1% by weight and preferably from about 0.5 to about 0.8% by weight, one or more emollients or emollient oils such as mineral oil, avocado oil, petrolatum, propylene glycol dicaprylate/dicaprate and isopropyl myristate in an amount within the range of from about, 10 to about 20% by weight and preferably from about 10 to about 15% by weight, one or more co-emulsifiers such as PEG 20 sorbitan monolaurate (Polysorbate 20), diethanolamine cetyl phosphate, glyceryl stearate, polyethylene glycol 100 stearate, and PEG 20 stearyl ether (Brij 78, Steareth 20) or PEG 150 distearate in an amount within the range of from about 0.1 to about 7% by weight and preferably from about 0.2 to about 5% by weight; one or more bodying agents such as stearic acid, glyceryl monostearate, and the like in an amount within the range of from about 1 to about 10% by weight and preferably from about 1 to about 5% by weight, optionally one or more sun screen agents such as octyl dimethyl p-aminobenzoic acid, octyl salicylate, benzophenone 3 and the like in an amount within the range of from about 0.5 to about 10% by weight and preferably from about 1 to about 5% by weight, and optionally one or more antioxidants such as dl-alpha-tocopherol in an amount within the range of from about 0.05 to about 0.5% by weight and preferably frm about 0.05 to about 0.2% by weight. In addition, the formulations of the invention may contain one or more fragrances, solubilizing agents and emulsifiers for the fragrances such as polyoxyethylene (13) octyl phenyl ether.

The actual structure and compositions of the test devices employed are disclosed in U.S. Pat. Nos. 3,814,668 (reducing sugar such as glucose), 3,438,737 (protein such as albumin), and 3,461,036, 3,427,225 and 3,395,082 (urea) and the subject matter thereof is incorporated herein by reference. As described in the above patents, the presence and concentration of each of the above actives may be detected by wetting one or more appropriate test strips, applying the test strips to the skin and observing color changes produced on the test strips.

The moisturizer composition may be prepared as follows.

Deionized water (diluent) together with glycerine and/or other water-soluble humectants, optionally one or more wetting agents, one or more actives such as glucose (and/or other reducing sugar), urea and/or protein, and optionally one or more thickeners, optionally one or more preservatives such as methyl paraben are mixed together to form a first mixture (A). Then, one or more water-insoluble humectants, emollients, thickeners, emulsifiers, as well as preservatives etc. are mixed together to form the oil phase or a second mixture (B) which is mixed with mixture (A) to form mixture (AB). A third phase formed of an aqueous solution of preservative and surfactant may be added to form the final mixture which is cooled to form the moisturizer composition.

The following Examples represent preferred embodiments of the present invention. All temperatures are expressed in degrees Centigrade unless otherwise indicated.

EXAMPLES 1 AND 2

Moisturizer formulations in the form of creams having the following compositions are prepared as described below.

| Ingredient | Parts by Weight | | |
|---|---|---|---|
| Example No. | 1 | 2 | Control |
| Blend A | | | |
| Deionized water (emollient) | 78.5 | 79.5 | 79 |
| Glycerine (humectant) | 2 | 2 | 2 |
| Methyl paraben (preservative) | 0.2 | 0.2 | 0.2 |
| Glucose (active) | 2 | — | — |
| Urea (active) | — | 1 | — |
| Blend B | | | |
| Octyl palmitate (emollient) | 5 | 5 | 5 |
| Dimethicone (emollient) | 2 | 2 | 2 |
| Polyethylene glycol 20 sorbitan monostearate (emulsifier) | 3 | 3 | 3 |
| Glyceryl monostearate and Sodium lauryl sulfate (bodying agent) (95:5) | 2 | 2 | 2 |
| Cetyl, stearyl alcohol and polyethylene glycol stearyl ether (1:1) (emulsifier) | 4.5 | 4.5 | 4.5 |
| Propyl paraben | 0.1 | 0.1 | 0.1 |
| Blend C | | | |
| Deionized water | 0.5 | 0.5 | 0.5 |
| Quaternium 15 (Dowicil 200) | 0.1 | 0.1 | 0.1 |

The ingredients of each of the three Blends A, B, and C were mixed while heating to form respective Blends A, B and C. Blend B was added to Blend A with homomixing for one hour. Blend C was then mixed with Blend AB for 15 minutes under slow speed mixing while heating to 75° C. The mixture was cooled to 30° C. to form the moisturizer formulations.

A glucose test strip is prepared as outlined in the Example in U.S. Pat. No. 3,814,668 and as set out below.

The following components are mixed, stepwise for the preparation of 100 ml of mix.

| Component | Quantity |
| --- | --- |
| (1) Potassium iodide | 1.0 g |
| (2) FD and C Blue No. 1 | 10.4 mg |
| (3) Distilled water | 53 ml |
| (4) Citric acid, anhydrous | 0.595 g |
| (5) Sodium citrate.2H$_2$O | 5.23 g |
| (6) Gantrez AN 139 copolymer of methyl vinyl ether and maleic anhydride (10% aqueous solution) | 10 ml |
| (7) Polyvinylpyrrolidone (10% aqueous solution) | 5 ml |
| (8) Peroxidase | [1]50 mg |
| (9) Glucose oxidase | [2]33 mg |

[1]3000 Worthington units/mcg
[2]1000 units/ml

Whatman 3 MM paper is impregnated with the above solution, allowed to drain and dried in a tunnel dryer set at 85° C. for 7 minutes. After removal from the drying tunnel, the impregnated paper is dipped into a solution of 0.85 grams of ethyl cellulose in 100 ml of benzene. After removal from this second impregnating solution, the paper is again dried, cut into small squares approximately 5 mm by 5 mm and attached to an end of a strip of fluid impervious plastic film 5 mm wide and approximately 6 cm long.

The Example 1 and Control moisturizer compositions are applied to the skin.

Excellent glucose quantitation is achieved employing a formulation as described above.

A urea test strip is prepared as outlined in Example 1 of U.S. Pat. No. 3,461,036.

The composition is formulated as follows:

| | |
| --- | --- |
| Gelatin | 0.5 g |
| Urease | 0.5 g |
| Acetamide | 1.0 g |
| 4% "Carbowax 4000" (polyethylene glycol) | 11.5 ml |
| 0.1 M ammonium citrate buffer (dibasic) | 2.5 ml |
| 1.6% aqueous solution bromothymol blue | 3.8 ml |

The gelatin is added to 11.5 ml of water and heated until completely dissolved. The remaining ingredients are combined and then mixed with the solution of gelatin until a clear solution is obtained. The temperature of the final solution is approximately 30° C. The solution pH is then adjusted to a pH of about 6.5 by the addition of small quantities of dilute sodium hydroxide. Paper strips measuring 2 inches by ¼ inch are then dipped in the solution and dried at a temperature of 85° C. The dried strips are then coated with a semi-permeable polymeric film by dipping them into a 1.25% solution of ethyl cellulose in benzene and air drying until the benzene is completely evaporated.

The Example 2 and Control A moisturizer compositions are applied to the skin.

Excellent urea quantitation is achieved employing a formuation as described above.

EXAMPLES 3 TO 7

Moisturizer formulations in the form of creams having the following compositions are prepared as described in Examples 1 and 2.

| Ingredient | Parts by Weight | | | | |
| --- | --- | --- | --- | --- | --- |
| Example No. | 3 | 4 | 5 | 6 | 7 |
| Blend A | | | | | |
| Deionized water (diluent) | 78.5 | 78.5 | 79 | 79.5 | 79 |
| Glycerine (humectant) | 2 | 2 | 2 | 2 | 2 |
| Methyl paraben (preservative) | 0.2 | 0.2 | 0.2 | 0.2 | 0.2 |
| Glucose (active) | 2 | — | 2 | — | 2 |
| Urea (active) | 1 | — | — | 1 | 1 |
| Albumin (active) | — | 1 | 1 | 1 | 1 |
| Blend B | | | | | |
| Octyl palmitate (emollient) | 5 | 5 | 5 | 5 | 5 |
| Dimethicone (emollient) | 2 | 2 | 2 | 2 | 2 |
| Polyethylene glycol 20 sorbitan monostearate (emulsifier) | 3 | 3 | 3 | 3 | 3 |
| Glyceryl monostearate and sodium lauryl sulfate (1:1) (bodying agent) | 2 | 2 | 2 | 2 | 2 |
| Cetyl, stearyl alcohol and polyethylene glycol (emulsifier) stearyl ether (1:1) | 4.5 | 4.5 | 4.5 | 4.5 | 4.5 |
| Propyl paraben | 0.1 | 0.1 | 0.1 | 0.1 | 0.1 |
| Blend C | | | | | |
| Deionized water | 0.5 | 0.5 | 0.5 | 0.5 | 0.5 |
| Quaternium 15 (Dowicil 200) | 0.1 | 0.1 | 0.1 | 0.1 | 0.1 |

A protein test strip is prepared as outlined in U.S. Pat. No. 3,438,737.

The compositions set out below in the Table are prepared as follows: a buffer solution is first prepared by mixing the sodium citrate, citric acid and water. The solution is then combined with the indicated amount of a 0.1% aqueous solution of tartrazine and the combination mixed with a solution comprising the indicated amounts of ethanol and tetrabromphenol blue. Strips of Eatman and Dikeman No. 641 filter paper are dipped into the various compositions, allowed to drain and dried at 100° C. for 11 minutes. When 40 square inches of the impregnated strip is extracted with 15 ml water, the strips exhibit substantially the same pH as that of the buffer solution. Upon contact with various solutions containing from 0 to 1000 mg percent of protein, the strips prepared from the test composition are capable of accurately detecting the quantity of protein present to a lower concentration limit of from about 5–10 mg percent. The hue change is from yellow or a slight off-yellow to blue with various intermediate hues depending on the amount of protein present in the solution.

| | Amount |
| --- | --- |
| Sodium citrate (g) | 10 |
| Citric Acid (g) | 14 |
| Water (ml) | 140 |
| Tetrabromphenol Blue (mg) | 48.5 |
| Ethanol (95%) (ml) | 48.5 |

| Amount of protein in solution (mg.-percent): | Hue of strip |
| --- | --- |
| 0 | Pyrethrum yellow (51) |
| 5–20 | Apple green (57) |
| 30 | Variscate green (66) |
| 100 | Turquoise green (72) |
| 300 | Turquoise blue (75) |
| 1000+ | Blue turquoise (78) |

The Examples 3 to 7 moisturizer composition are applied to different test subjects. The test devices for glucose and urea described in Examples 1 and 2 and the test device for protein set out above are wetted with water and contacted with skin treated with appropriate moisturizer compositions. For example, the protein (albumin) test device is used for testing subjects treated with Examples 4, 5, 6 and 7 and Control compositions, the glucose device is used for testing subjects treated with Examples 3, 5 and 7 compositions and the urea device is used for testing subjects treated with Examples 3, 6 and 7 compositions.

The results obtained from the Examples 4, 5, 6 and 7 subjects are that after 1 minute, the amount of protein is shown as 0 for the Control A device and satisfactory for the Examples 4, 5, 6 and 7 subjects since the Examples 4, 5, 6 and 7 test strips turned blue turquoise.

The glucose test strips for the Examples 3, 5, and 7 subjects turn brown and the urea test strips for the Examples 3, 6 and 7 subjects turn characteristic color for urea.

What is claimed is:

1. A method for determining the presence of moisturizing substances on skin, which comprises providing a moisturizing composition which includes an active material capable of binding with water to form a complex, applying the moisturizing composition to desired areas of the skin to form a film or coating which includes such complex and which inhibits moisture loss from the skin, and subsequently testing skin previously treated with such moisturizing composition for the presence of the active material remaining on the previously treated skin, the presence of which active material is directly correlated to the amount of moisturizer composition remaining on the skin.

2. The method as defined in claim 1 wherein the active material is a protein, urea and/or glucose and/or other reducing sugar or carbohydrate.

3. The method as defined in claim 2 wherein the moisturizer composition contains from about 0.1 to about 10% by weight protein, from about 0.1 to about 10% by weight urea and/or from about 0.1 to about 10% by weight glucose.

4. The method as defined in claim 3 wherein the moisturizer composition contains protein in the form of albumin.

5. The method as defined in claim 3 wherein the moisturizer composition contains urea.

6. The method as defined in claim 3 wherein the moisturizer composition contains glucose.

7. The method as defined in claim 3 wherein the moisturizer composition contains both protein and urea, or both protein and glucose or both glucose and urea, or all of protein, urea and glucose.

8. The method as defined in claim 2 wherein the moisturizer composition includes, in addition, one or more thickeners, one or more humectants, one or more emollients, one or more preservatives, one or more diluents and one or more emulsifiers.

9. The method as defined in claim 2 wherein the moisturizer composition contains from about 40 to about 90% by weight water.

10. The method as defined in claim 2 wherein the testing step comprises wetting a test strip specific for the active material contained in the moisturizer composition and applying said wet test strip to the skin.

11. The method as defined in claim 10 wherein each test strip is specific for one active materials.

* * * * *